United States Patent
Wang et al.

(10) Patent No.: US 10,043,269 B2
(45) Date of Patent: Aug. 7, 2018

(54) MEDICAL IMAGE PROCESSING APPARATUS, MEDICAL IMAGE DIAGNOSTIC APPARATUS, MEDICAL IMAGE PROCESSING METHOD, AND ULTRASONIC IMAGE PROCESSING METHOD

(71) Applicant: Toshiba Medical Systems Corporation, Otawara-shi (JP)

(72) Inventors: Yanhua Wang, Beijing (CN); Yao Cong, Otawara (JP); Yanli Wang, Beijing (CN)

(73) Assignee: Toshiba Medical Systems Corporation, Otawara-shi (JP)

( * ) Notice: Subject to any disclaimer, the term of this patent is extended or adjusted under 35 U.S.C. 154(b) by 79 days.

(21) Appl. No.: 15/009,190

(22) Filed: Jan. 28, 2016

(65) Prior Publication Data
US 2016/0260209 A1    Sep. 8, 2016

(30) Foreign Application Priority Data

Mar. 3, 2015   (CN) .......................... 2015 1 0095321
Sep. 29, 2015  (JP) ................................. 2015-191599

(51) Int. Cl.
*A61B 8/08*       (2006.01)
*G06T 7/00*       (2017.01)
(Continued)

(52) U.S. Cl.
CPC .......... *G06T 7/0012* (2013.01); *A61B 5/1128* (2013.01); *A61B 6/469* (2013.01);
(Continued)

(58) Field of Classification Search
CPC .................... G06T 7/0012; G06T 7/60; G06T 2207/30044; G06T 2207/10132;
(Continued)

(56) References Cited

U.S. PATENT DOCUMENTS 5,817,035 A * 10/1998 Sullivan ............. A61B 5/02411
                                                              600/500
6,185,320 B1 * 2/2001 Bick ...................... G06K 9/482
                                                              382/132
(Continued)

FOREIGN PATENT DOCUMENTS

JP         2012-213604         11/2012

*Primary Examiner* — Carol Wang
(74) *Attorney, Agent, or Firm* — Oblon, McClelland, Maier & Neustadt, L.L.P.

(57) ABSTRACT

A medical image processing apparatus includes a setting unit, a tracking unit, and a calculation unit. The setting unit is configured to set a first region of interest in at least one of a plurality of medical images. The tracking unit is configured to carry out first tracking processing of tracking the motion of the first region of interest between the medical images and second tracking processing of tracking the motion of a second region of interest, different from the first region of interest, between the medical images. The calculation unit is configured to calculate the motion of the second region of interest with respect to the first region of interest by using the result of the first tracking processing and the result of the second tracking processing.

13 Claims, 5 Drawing Sheets

(51) Int. Cl.
*G06K 9/52* (2006.01)
*G06T 7/60* (2017.01)
*A61B 5/11* (2006.01)
*A61B 6/00* (2006.01)
*A61B 8/10* (2006.01)
*G06K 9/46* (2006.01)
*A61B 8/00* (2006.01)
*A61B 5/055* (2006.01)

(52) U.S. Cl.
CPC ............ *A61B 6/486* (2013.01); *A61B 6/5211* (2013.01); *A61B 8/08* (2013.01); *A61B 8/0866* (2013.01); *G06K 9/52* (2013.01); *G06T 7/60* (2013.01); *A61B 5/055* (2013.01); *A61B 8/085* (2013.01); *A61B 8/10* (2013.01); *A61B 8/469* (2013.01); *A61B 8/5223* (2013.01); *A61B 2503/02* (2013.01); *G06K 2009/4666* (2013.01); *G06T 2207/10132* (2013.01); *G06T 2207/30044* (2013.01)

(58) Field of Classification Search
CPC  G06K 9/52; G06K 2009/4666; A61B 6/5211; A61B 6/469; A61B 6/486; A61B 5/1128; A61B 5/055; A61B 8/08; A61B 8/0866; A61B 8/469; A61B 8/5223; A61B 8/085; A61B 8/10; A61B 2503/02
See application file for complete search history.

(56) References Cited

U.S. PATENT DOCUMENTS

| | | | |
|---|---|---|---|
| 9,254,115 B2* | 2/2016 | Abe | A61B 8/08 |
| 2009/0270732 A1* | 10/2009 | Abe | A61B 8/0883 600/443 |
| 2010/0016744 A1* | 1/2010 | Brost | A61B 8/02 600/511 |
| 2010/0195887 A1* | 8/2010 | Abe | A61B 8/08 382/131 |
| 2013/0182935 A1* | 7/2013 | Wang | G06K 9/3233 382/133 |
| 2014/0119610 A1* | 5/2014 | Funaya | A61B 8/469 382/107 |
| 2014/0148695 A1* | 5/2014 | Funaya | A61B 8/5215 600/437 |

* cited by examiner

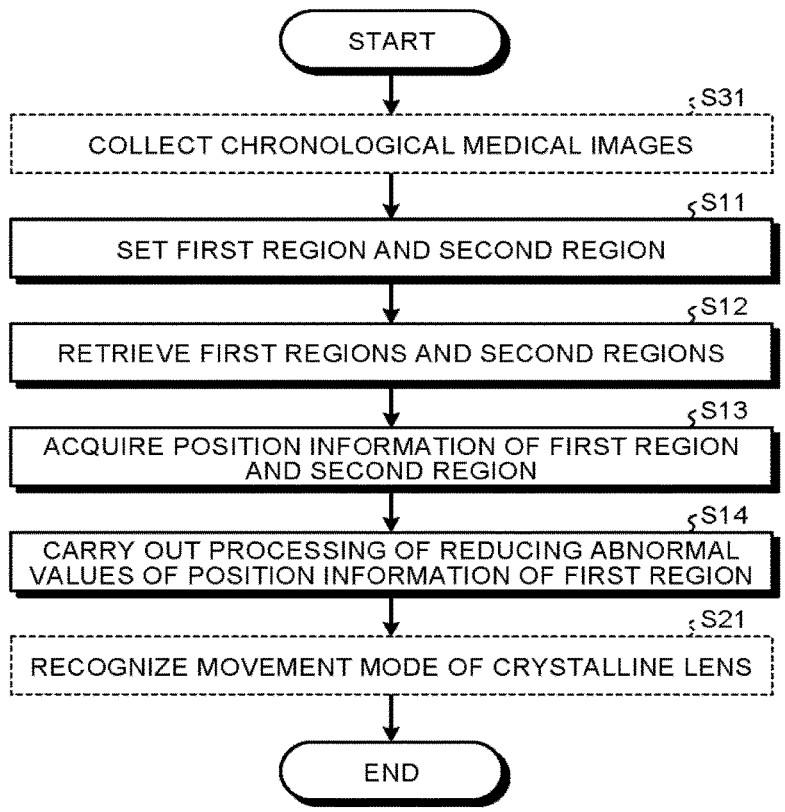
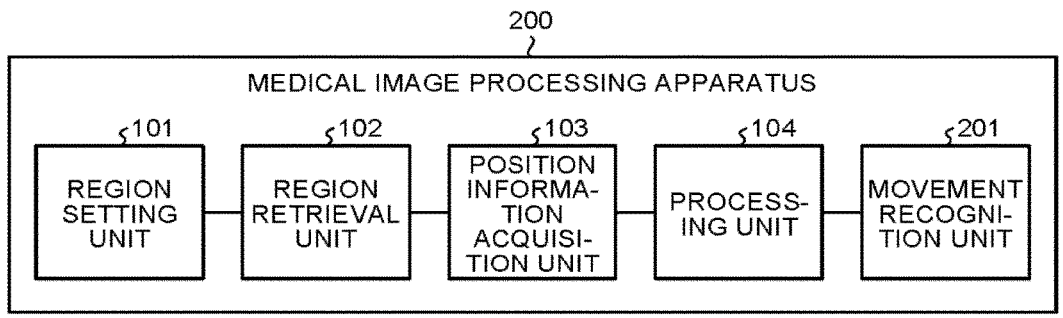

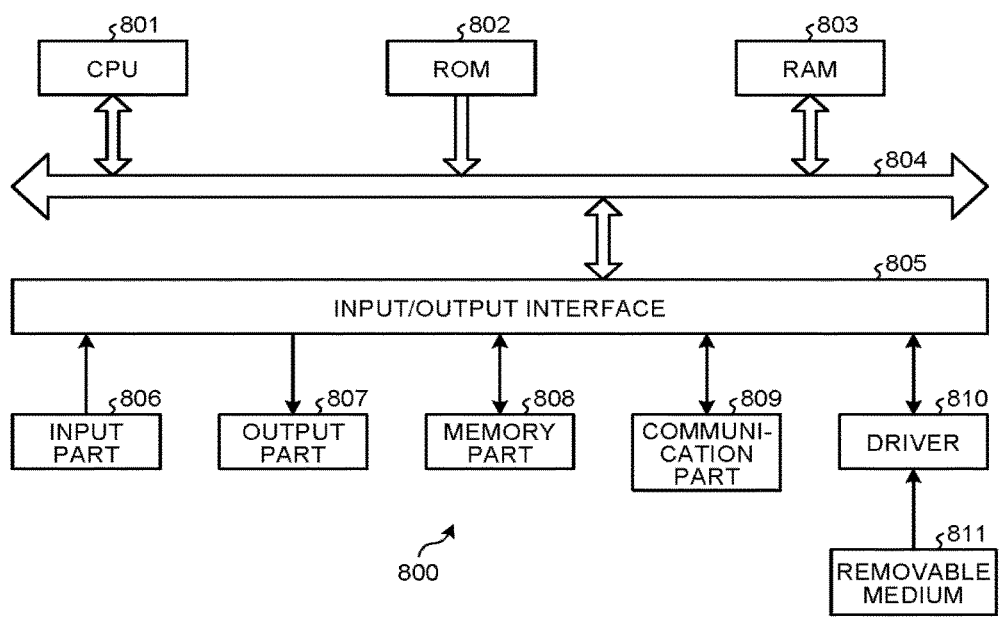

MEDICAL IMAGE PROCESSING APPARATUS, MEDICAL IMAGE DIAGNOSTIC APPARATUS, MEDICAL IMAGE PROCESSING METHOD, AND ULTRASONIC IMAGE PROCESSING METHOD

CROSS-REFERENCE TO RELATED APPLICATIONS

This application is based upon and claims the benefit of priority from Chinese Patent Application No. 201510095321.9, filed on Mar. 3, 2015; and Japanese Patent Application No. 2015-191599, filed on Sep. 29, 2015, the entire contents of all of which are incorporated herein by reference.

FIELD

Embodiments described herein relate generally to a medical image processing apparatus, a medical image diagnostic apparatus, a medical image processing method, and an ultrasonic image processing method.

BACKGROUND

When imaging a specific structure in a subject, it is needed in some cases to analyze dynamic motions of the specific structure, in other words, it is needed in some cases to track the specific structure within a period of time. This processing can be realized by, for example, acquiring a series of chronological images aiming at the region where the specific structure exists and recognizing the form of the specific structure in each of the images. When recognizing the specific structure, it is possible to adopt for example a manner of manually marking or automatically marking.

However, on one hand, it is impractical to manually mark the specific structure when there are a great number of images; on the other hand, it is difficult to accurately recognize the position of the specific structure in each image automatically because the various limitations to imaging conditions and the inherent characteristics of the specific structure may lead to the low resolution of the images obtained and the unnoticeable characteristics of the specific structure. Therefore, an apparatus and a method are desired that enable automatically tracking a specific structure in a medical image rapidly and accurately.

BRIEF DESCRIPTION OF THE DRAWINGS

FIG. 4 is a flowchart illustrating a medical image processing method and a medical diagnostic method according to the first embodiment;

FIG. 5 is a block diagram showing the structure of a medical image processing apparatus according to a second embodiment;

FIG. 8 is a block diagram exemplifying the structure of a computer capable of realizing the embodiments.

DETAILED DESCRIPTION

Figure 1:
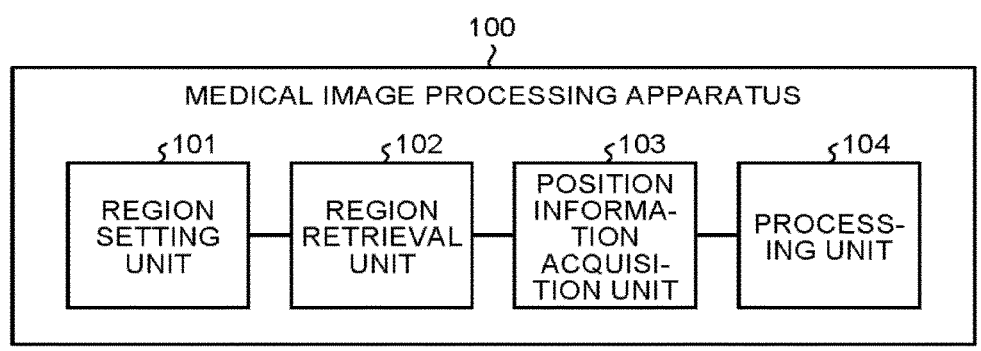
FIG. 1 is a block diagram showing the structure of a medical image processing apparatus according to a first embodiment.

According to an embodiment, a medical image processing apparatus includes processing circuitry. The processing circuitry is configured to set a first region of interest in at least one of a plurality of medical images. The processing circuitry is configured to carry out first tracking processing of tracking the motion of the first region of interest between the medical images and second tracking processing of tracking the motion of a second region of interest, different from the first region of interest, between the medical images. The processing circuitry is configured to calculate the motion of the second region of interest with respect to the first region of interest by using the result of the first tracking processing and the result of the second tracking processing.

An overview of embodiments will be described below with reference to the accompanying drawings. The overview is not to be construed as determining a key or important area of the present application and limiting the scope of the present application. The overview, i.e., simple description, of the embodiments is aimed at introduction of the following further-detailed description. The present application relates generally to the field of medical image processing and, specifically, to a medical image processing apparatus, a medical image processing method, a medical image diagnostic apparatus, and a medical image diagnostic method that enable tracking a specific structure in chronological images to acquire the position of the specific structure in each of the images.

In accordance with an aspect of the present embodiments, a medical image processing apparatus is provided, comprising: a region setting unit configured to set, aiming at at least one of a plurality of chronological medical images corresponding to a region in a subject containing a specific structure, a first region containing the specific structure and a second region located in the first region and representing the specific structure; a region retrieval unit configured to retrieve, based on the first and the second regions set by the region setting unit, the first regions and the second regions in the rest of the plurality of medical images excluding those in which the first and the second regions are set by the region setting unit; a position information acquisition unit configured to acquire position information of the first region set by the region setting unit, position information of the first regions retrieved by the region retrieval unit, position information of the second region set by the region setting unit and position information of the second regions retrieved by the region retrieval unit; and a processing unit configured to carry out, for at least part of the position information of the first region acquired by the position information acquisition unit, a processing of reducing abnormal values of the chronological change of the position information of the first region acquired by the position information acquisition unit and acquire, for each time point, the position information of the second region with respect to the position information of the first region containing the position information subjected to the processing.

In accordance with another aspect of the present embodiments, a medical image processing method is provided, comprising: setting, aiming at at least one of a plurality of chronological medical images corresponding to a region in a subject containing a specific structure, a first region containing the specific structure and a second region located in the first region and representing the specific structure; retrieving, based on the set first and second regions, the first regions and the second regions in the rest of the plurality of medical images excluding those in which the first and the second regions are set; acquiring position information of the set first region, position information of the retrieved first regions, position information of the set second region and position information of the retrieved second regions; and carrying out, for at least part of the position information of the first region acquired, a processing of reducing abnormal values of the chronological change of the position information of the first region and acquiring, for each time point, the position information of the second region with respect to the position information of the first region containing the position information subjected to the processing.

In accordance with still another aspect of the present embodiments, a medical image diagnostic apparatus is provided, comprising: a medical image collection unit configured to collect a plurality of chronological medical images corresponding to a region in a subject containing a specific structure; a region setting unit configured to set, aiming at at least one of the plurality of medical images, a first region containing the specific structure and a second region located in the first region and representing the specific structure; a region retrieval unit configured to retrieve, based on the first and the second regions set by the region setting unit, the first regions and the second regions in the rest of the plurality of medical images excluding those in which the first and the second regions are set by the region setting unit; a position information acquisition unit configured to acquire position information of the first region set by the region setting unit, position information of the first regions retrieved by the region retrieval unit, position information of the second region set by the region setting unit and position information of the second regions retrieved by the region retrieval unit; and a processing unit configured to carry out, for at least part of the position information of the first region acquired by the position information acquisition unit, processing of reducing abnormal values of the chronological change of the position information of the first region acquired by the position information acquisition unit and acquire, for each time point, the position information of the second region with respect to the position information of the first region containing the position information subjected to the processing.

In accordance with yet another aspect of the present embodiments, a medical image diagnostic method is provided, comprising: collecting a plurality of chronological medical images corresponding to a region in a subject containing a specific structure; setting, aiming at at least one of the plurality of medical images, a first region containing the specific structure and a second region located in the first region and representing the specific structure; retrieving, based on the set first and second regions, the first regions and the second regions in the rest of the plurality of medical images excluding those in which the first and the second regions are set; acquiring position information of the set first region, position information of the retrieved first regions, position information of the set second region and position information of the retrieved second regions; and carrying out, for at least part of the position information of the first region acquired, processing of reducing abnormal values of the chronological change of the position information of the first region and acquiring, for each time point, the position information of the second region with respect to the position information of the first region containing the position information subjected to the processing.

Further, in accordance with yet still another aspect of the present embodiments, computer programs for realizing the foregoing medical image processing method and the foregoing medical image diagnostic method are provided.

Further, in accordance with still further another aspect of the present embodiments, computer program products are provided which are in the form of a medium at least readable to a computer and on which computer program codes for realizing the foregoing medical image processing method and the foregoing medical image diagnostic method are recorded.

In the medical image processing apparatus and method and the medical image diagnostic apparatus and method provided herein, the rough tracking of a specific structure is corrected by reducing the abnormal chronological change of a first region containing the specific structure, and the change of the position information of the specific structure obtained based on the corrected rough tracking is relatively accurate, thus improving the accuracy of automatic tracking.

The following further description with reference to the accompanying drawings allows easy understanding of the purpose, characteristics, and merits of the embodiments. The configurations in the drawings show the principle of the embodiments only. The same or similar technical features or configuration between drawings are expressed with the same or similar notation.

With reference to the accompanying drawings, the embodiments will be described below. The elements and features described in an accompanying drawing or embodiment can be combined with those shown in one or more other accompanying drawings or embodiments. It should be noted that for the sake of clarity, representation and description of the components and processing that are unrelated to the embodiments but well known to those of ordinary skilled in the art are omitted in accompanying drawings and descriptions.

First Embodiment

FIG. 1 is a block diagram showing the configuration of a medical image processing apparatus 100 according to a first embodiment. As shown in FIG. 1, the medical image processing apparatus 100 includes a region setting unit 101, a region retrieval unit 102, a position information acquisition unit 103, and a processing unit 104. The region setting unit 101 is referred to also as a setting unit. The region retrieval unit 102 and the position information acquisition unit 103 are collectively referred to also as a tracking unit. The processing unit 104 is referred to also as a calculation unit or a correction unit. The processing performed by each of the above-listed units of the medical image processing apparatus 100 enables accurate tracking of a specific structure in medical image collected chronologically, which can improve the accuracy of analyzing the specific structure.

As analysis of the specific structure, for example, there is analysis of the degree of the growth of a fetus based on the motion of the eyeballs. For example, the eyeballs of a fetus take rapid eye movement (REM) and slow eye movement (SEM) at a predetermined ratio. It is known that, when there is a disorder in the brain of the fetus, the motion of the eyeballs reduces and the proportion of SEM increases. Accordingly, analyzing the motion of the eyeballs of the fetus allows an analysis of the degree of the growth of the brain of the fetus; however, in order to analyze the motion of the eyeballs of the moving fetus, only tracking the position of the eyeballs is insufficient. In other words, in order to accurately track the eyeballs of the fetus, tracking of the eyeballs in consideration of the motion of the fetus in the mother is required.

In the medical image processing apparatus 100, in order to track the eyeballs in consideration of the motion of the fetus in the mother, the region setting unit 101 sets a first region of interest (first region) with respect to at least one of a plurality of medical images. The region retrieval unit 102 and the position information acquisition unit 103 performs first tracking processing of tracking the motion of the first region of interest between the medical images and second tracking processing of tracking the motion of a second region of interest (second region) different from the first region of interest between the medical images. The processing unit 104 calculates the motion of the second region of interest with respect to the first region of interest by using the result of the first tracking processing and the second tracking processing. The processing unit 104 executes a first correction processing of correcting the result of the first tracking processing and the second correction process of correcting the result of the second tracking processing by using the first correcting process and calculates the motion of the second region of interest with respect to the first region of interest by using the results of the first correcting process and the second correction process.

More specifically, the region setting unit 101 is configured to set, aiming at at least one of a plurality of chronological medical images corresponding to a region in a subject containing a specific structure, a first region containing the specific structure and a second region located in the first region and representing the specific structure. The region retrieval unit 102 is configured to retrieve, based on the first and second regions set by the region setting unit 101, the first regions and the second regions in the rest of the medical images excluding those in which the first and second regions are set by the region setting unit 101. The position information acquisition unit 103 is configured to acquire position information of the first region set by the region setting unit 101, position information of the first regions retrieved by the region retrieval unit 102, position information of the second region set by the region setting unit 101 and position information of the second regions retrieved by the region retrieval unit 102. The processing unit 104 is configured to carry out, for at least part of the position information of the first region acquired by the position information acquisition unit 103, processing of reducing abnormal values of the chronological change of the position information of the first region acquired by the position information acquisition unit 103 and acquire, for each time point, the position information of the second region with respect to the position information of the first region containing the position information subjected to the processing.

The subject may be, for example, a human body or an animal body, and the foregoing medical image processing apparatus 100 may be used to process a plurality of medical images acquired by chronologically shooting or scanning a specific part of the subject for a period of time. The specific part contains, for example, a specific structure to be observed. Thus, the medical images contain regions reflecting the states of the specific structure at different time points.

By operating the foregoing medical image processing apparatus 100, the position of a specific structure in each medical image can be obtained, in other words, the movement track or change of the specific structure can be tracked and analyzed.

The foregoing medical images are, for example, ultrasonic images collected through Ultrasonic (UL) diagnosis. However, the approach for obtaining the medical images may also be X-ray imaging diagnosis, Computed Tomography (CT), Magnetic Resonance Imaging (MRI), Positron Emission Tomography (PET) and so on, but not limited to ultrasonic diagnosis.

The region setting unit 101 sets the first region and the second region for at least one of the plurality of medical images, for example, the medical image chronologically ranked first, wherein the first region contains the specific structure, and the second region is located in the first region and represents the specific structure. In other words, the area of the second region is generally smaller than that of the first region so that the specific structure can be positioned more accurately in the medical images. In other words, setting the two types of regions, i.e., the first region and the second region, and analyzing the position of the second region with respect to the first region in the chronological medical images enable analyzing the motion of the specific structure in the target accompanying motion.

Figure 2:
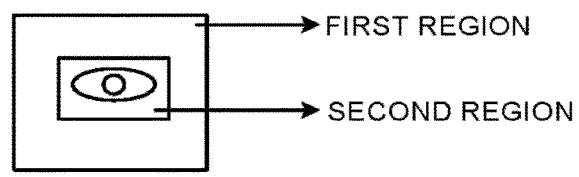
FIG. 2 is a schematic diagram illustrating the setting of a first region and a second region according to the first embodiment.

As an example, the structure may be an eyeball or crystalline lens of a fetus in the subject, the first region is a region containing the eyeball or a region representing the eyeball, and the second region is located in the first region and used to represent the position of the eyeball more accurately. FIG. 2 is a diagram illustrating the setting of the first region and the second region according to the first embodiment. FIG. 2 is a schematic diagram illustrating the setting of the first region and the second region in an example in which the structure is an eyeball, and in FIG. 2, the oval represents an eyeball and the circle in the oval represents a crystalline lens.

It should be noted that although square-shaped in FIG. 2, the first and second regions may take various shapes such as circle, polygons and irregular shapes but not limited thereto, depending on the shape of the structure or the requirement of image processing. Besides, although only one first region and only one second region are shown in FIG. 2, there may be more than one first region and more than one second region.

After the first and second regions are set by the region setting unit 101, the region retrieval unit 102 retrieves the first and second regions in the rest of medical images not subjected to the setting so as to obtain corresponding first and second regions in each medical image. The region retrieval unit 102 may recognize the first regions and the second regions in the rest of medical images using various recognition methods. Moreover, when the second region is retrieved, the retrieval may be, for example, limited to being carried out in the first region retrieved. When the collected chronological medical images are, for example, two-dimensional ultrasonic images, the specific structure may be out of the scanning cross-section. For example, when the fetus moves during ultrasonic scanning, the eyeball may be out of the scanning cross-section. For this reason, retrieving the first region first from the ultrasonic images acquired chronologically enables extracting images containing the specific structure (image where the cross-section has not shifted) from the ultrasonic images. Carrying out retrieval of the second region to the extracted image enables more accurate detection of the specific structure.

As an example, the region retrieval unit 102 may perform the retrieval through template matching. In other words, the region retrieval unit 102 takes the set first region and second region as templates to retrieve matching regions in the rest of medical images and takes the retrieved regions as corresponding first and second regions. In a case where the first region (and the second region) is set aiming at a plurality of medical images, the region retrieval unit 102 may perform the retrieval by, for example, taking each of the first regions (and the second regions) as a template.

Alternatively, the region retrieval unit 102 may adopt another feature recognition method, for example, an edge feature recognition method or the like. Specifically, the region retrieval unit 102 may acquire the features of the set first and second regions first, and then use the features to retrieve, in each of the rest of the medical images, to obtain regions matched with the features as corresponding first and second regions.

Sequentially, the position information acquisition unit 103 acquires the position information of the first region and the second region in each medical image. The position information may be the absolute position coordinates or the relative position information of the first region and the second region in the subject. The position information acquisition unit 103 is capable of acquiring information on the degree of the change of the relative positions between the first region and the second region. For example, the position information acquisition unit 103 is capable of calculating, for the change of the position of the second region with respect to the first region, the distance having changed (moving distance) or the speed of change (moving speed).

In an example, the position information acquisition unit 103 takes the position information of the first and second regions in a medical image obtained at a predetermined time point as reference position information, and acquires the position information of the first regions and the second regions in the rest of medical images with respect to the reference position information. The medical image obtained at a predetermined time point corresponds to one of the medical images, for example, a certain point in the medical image may be used as the origin of coordinates to obtain the coordinates of the first and second regions in the medical image and those of the first and second regions in the rest of medical images with respect to this point.

Next, the processing unit 104 carries out correction processing aiming at at least part of the position information of the first region acquired, that is, the processing unit 104 reduces the abnormal values of the chronological change of the position information. This is because that the effect of noise and the like leads to the deviation of the position of the first region retrieved by the region retrieval unit 102 from a correct position, that is, leads to a tracking error. The tracking error shows up as abnormal values of the chronological change of the position information, and these abnormal values do not meet the movement rule of the structure. For this sake, the processing unit 104 carries out the processing of reducing these abnormal values (hereinafter referred to as the correction processing) so as to obtain more accurate position information of the first region.

Specifically, the processing unit 104 may carry out processing of reducing the frequency component of the chronological change of the position information of the first region as the processing of reducing the abnormal values of the chronological change of the position information of the first region.

For example, the processing unit 104 may be configured to carry out the foregoing processing by filtering a high-frequency component using a low-pass filter. This is because that the position information of the wrongly tracked first region is represented as a high-frequency component in the frequency domain. The filtering of the high-frequency component using a low-pass filter, which is equivalent to the smoothing of the position information of the first region in a time domain, can reduce the abnormal values.

As an example, the processing unit 104 carries out, aiming at the chronological change of the position information of the first region, Fourier fitting processing as the processing of reducing the abnormal values of the chronological change of the position information of the first region. For example, the processing unit 104 may be configured to carry out the Fourier fitting processing aiming at the components of the position information of the first region in each direction. In a case where the medical images are two-dimensional images, the Fourier fitting may be carried out aiming at, for example, the component in the horizontal direction and the component in the vertical direction. It should be noted that processing mode described herein is merely exemplary but not limitative.

Furthermore, the processing unit 104 may acquire, for each time point, the position information of the second region with respect to the position information of the first region containing the position information subjected to the processing. Specifically, the processing unit 104 may acquire the position information of the second region in a local area of the first region subjected to the correction processing.

As an example, the processing unit 104 may re-retrieve the second region in the first region subjected to the correction processing and acquire the position information of the second region re-retrieved.

Taking the structure being the crystalline lens of a fetus in the subject as an example, as the crystalline lens is located within an eyeball, the movement information of the crystalline lens can be obtained by tracking the eyeball. However, due to the inclusion of various kinds of movements such as the breathing movement of the mother, the movement of the fetus and the movement of the eyeball and the effect of the moving of a scanning operator etc., as well as the effect of noise in the actually obtained medical image, it is complicated and difficult to track the eyeball in the medical image, moreover, the movement track of the eyeball is unpredictable. The eyeball can be manually marked in a short video, for example, a video of several frames. However, it becomes impractical to manually mark the eyeball in a long video which lasts for, for example, several or even dozens of minutes. Especially when the medical image is taken using an ultrasonic diagnostic imaging apparatus, as the signal-to-noise ratio of the obtained image is relatively low, it is more difficult to track the eyeball automatically.

In the application of the medical image processing apparatus 100 provided in an embodiment, with the use of the region setting unit 101, the first region may be set to be a region containing an eyeball, and the second region may be set to be a region representing a crystalline lens. The first regions and the second regions in the rest of medical images are obtained by using the region retrieval unit 102, the position information of the first and second regions in each of the medical images is obtained by using the position information acquisition unit 103; and the position information of the first region having less abnormal values is obtained through the processing of the processing unit 104, for example, the Fourier fitting of the processing unit 104 for the position information of the first region changing with time, thereby obtaining, for each time point, the position information of the second region with respect to the position information of the first region containing the position information subjected to the processing, for example, the information of the chronological change of the relative position of the second region with respect to the first region may be further obtained. In this way, the information of the position change of the crystalline lens with respect to the eyeball is obtained so that the movement mode (to be described later in detail) of the crystalline lens can be recognized.

Figure 3A:
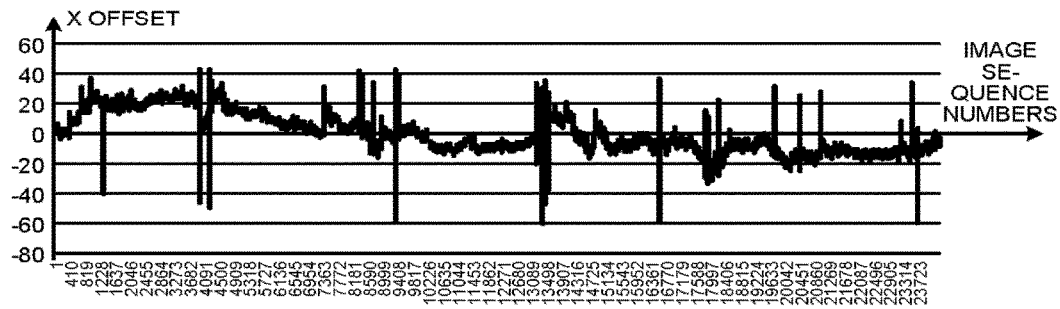
FIG. 3A is a graph exemplifying an exemplary processing result according to the first embodiment.
Figure 3B:
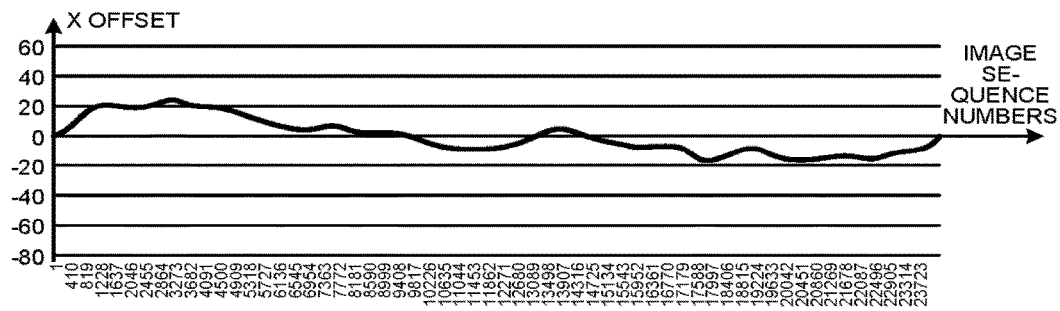
FIG. 3B is a graph exemplifying an exemplary processing result according to the first embodiment.
Figure 3C:
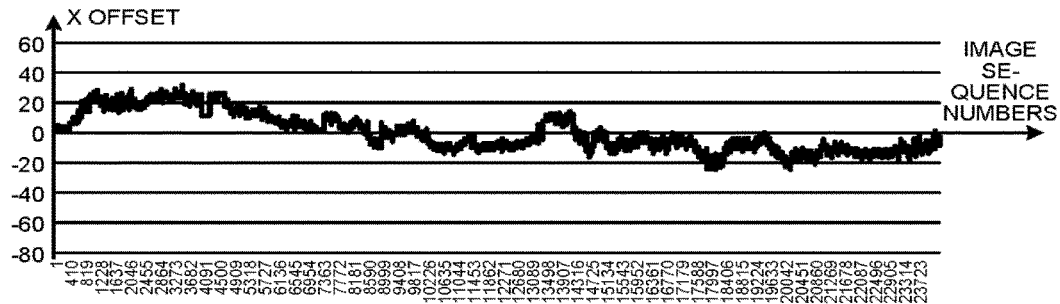
FIG. 3C is a graph exemplifying an exemplary processing result according to the first embodiment.

FIGS. 3A to 3C are graphs showing exemplary processing results according to the first embodiment. FIG. 3A to FIG. 3C are graphs showing the processing results of an example of the tracking on a series of chronological medical images which are acquired using an Ultrasonic (UL) diagnostic imaging apparatus and in which the eyeball region of a fetus in the subject is included. In these graphs, the horizontal axis represents image sequence numbers, that is, a time axis, and the longitudinal axis represents the offset of the first region in each image with respect to a reference position in an X direction (that is, the horizontal direction). In this example, the curve in FIG. 3A represents the chronological change of the position of the first region acquired by the position information acquisition unit 103, and that in FIG. 3B represents the chronological change of the position of the first region corrected by the processing unit 104 through Fourier fitting. As shown in FIG. 3B, it can be seen that some peaks in the movement tracks are removed through the Fourier fitting. For example, the rapid change of the pattern due to, for example, the abnormal values are reduced and are estimated based on neighbor motions. The curve in FIG. 3C represents the chronological change of the position of the second region with respect to the corrected position of the first region acquired by the processing unit 104.

It can be seen that the curve of FIG. 3C which shows the chronological change of the position of the second region is relatively smooth and reflects details of a movement. As described above, analyzing the chronological change of the position of the second region after removing the rapid pattern change can further improve the analysis accuracy. It should be appreciated that the crystalline lens of a fetus is merely an example of the structure, and the medical image processing apparatus disclosed herein is not limited to applying to this. According to the description of FIGS. 3A to 3C, the offset in the X direction (the horizontal direction) is taken as an example; however, embodiments are not limited to this. For example, the offset in a Y direction (the vertical direction) may be used.

Apparently, some processing or methods are also disclosed in the foregoing description of the medical image processing apparatus disclosed herein. When not overlapping those described above, the methods will be described in detail below. However, it should be noted that these methods, although disclosed during the process of describing the medical image processing apparatus, do not necessarily employ the foregoing components or are not necessarily executed by the foregoing components. For example, embodiments of the medical image processing apparatus may be partially or totally implemented as hardware and/or firmware, and the medical image processing method discussed below may also be wholly implemented as a computer-executable program, although these methods can also be implemented as the hardware and/or firmware of the medical image processing apparatus.

FIG. 4 is a flowchart illustrating a medical image processing method according to the first embodiment, and the medical image processing method includes: setting, aiming at at least one of a plurality of chronological medical images corresponding to a region in a subject containing a specific structure, a first region containing the specific structure and a second region located in the first region and representing the specific structure (S11); retrieving, based on the set first and second regions, the first regions and the second regions in the rest of the medical images excluding those in which the first and second regions are set (S12); acquiring position information of the set first region, position information of the retrieved first regions, position information of the set second region and position information of the retrieved second regions (S13); and carrying out, for at least part of the position information of the first region acquired, processing of reducing the abnormal values of the chronological change of the position information of the first region and acquiring, for each time point, the position information of the second region with respect to the position information of the first region containing the position information subjected to the processing (S14).

In Step S12, retrieval through template matching may be executed. In Step S13, the position information of the first and second regions in a medical image obtained at a predetermined time point may be used as reference position information, and the position information of the first regions and the second regions in the rest of medical images with respect to the reference position information may be acquired.

In Step S14, processing of reducing the frequency component of the chronological change of the position information of the first region may be performed as the processing of reducing the abnormal values of the chronological change of the position information of the first region. As an example, in Step S14, processing through Fourier fitting may be performed aiming at the chronological change of the position information of the first region as the processing of reducing the abnormal values of the chronological change of the position information of the first region.

The plurality of medical images may be, for example, ultrasonic images collected through ultrasonic diagnosis. The structure may be, for example, the eyeball or crystalline lens of a fetus in the subject, and the first region may be a region containing the eyeball or a region representing the eyeball.

More specific details of each step of the foregoing method and more possible steps of the foregoing method may be understood with reference to the foregoing description of each component in the medical image processing apparatus disclosed herein and are therefore not described here repeatedly.

By setting a first region and a second region, correcting the chronological position information of the first region and determining the position information of the second region based on the result of the correction, the foregoing medical image processing apparatus or the medical image processing method can accurately obtain the position of the specific structure in each medical image automatically to automatically track the movement track of the structure.

Second Embodiment

In the foregoing embodiment, the structure is the crystalline lens of a fetus in the subject. As stated in the first embodiment, through the processing of each component in the medical image processing apparatus 100, the position information of the second region can be obtained for each time point with respect to the position information of the first region containing the position information subjected to the processing of the processing unit 104.

FIG. 5 is a block diagram showing the configuration of a medical image processing apparatus according to a second embodiment. As shown in FIG. 5, in addition to each component of the medical image processing apparatus 100, a medical image processing apparatus 200 according to the second embodiment further includes a movement recognition unit 201 configured to recognize, in a case where the structure is the crystalline lens, the movement mode of the crystalline lens based on the chronological change of the position information of the second region with respect to the position information of the first region containing the position information subjected to the processing of the processing unit 104. The movement recognition unit 201 is referred to also as a recognition unit.

The movement mode of the crystalline lens includes, but is not limited to Rapid Eyeball Movement (REM) and Slow Eyeball Movement (SEM). By recognizing the movement mode of the crystalline lens, the function of the central nervous of the fetus can be reflected.

In an example, the movement recognition unit 201 can recognize the movement mode of the crystalline lens based on at least one of the change of the displacement of the crystalline lens with respect to the eyeball and the change of the angle of the crystalline lens with respect to the eyeball. For example, the movement recognition unit 201 recognizes the movement mode based on the moving distance and the moving speed calculated by the position information acquisition unit 103.

As stated above, when the first region is a region containing an eyeball and the second region is a region representing a crystalline lens, the processing unit 104 can obtain the position information of the second region with respect to the first region, and the movement recognition unit 201 can recognize the movement mode of the crystalline lens based on the information of chronological change of the relative position.

According to another embodiment, in a case where the first region is a region containing an eyeball and the second region is also a region containing an eyeball, the movement recognition unit 201 may further search the second region for the region where a crystalline lens exists to obtain the change of the position and/or the angle of the crystalline lens with respect to the eyeball to recognize the movement mode of the crystalline lens. The search process may be conducted through, for example, template matching or feature recognition.

A medical image processing method is also disclosed in the description of the medical image processing apparatus provided in the embodiment. Return to refer to FIG. 4, as shown by the dashed block shown in FIG. 4, in a case where the structure is a crystalline lens, in addition to Steps S11-S14, the foregoing medical image processing method may further include Step 321 of recognizing the movement mode of the crystalline lens based on the chronological change of the position information of the second region with respect to the position information of the first region containing the position information subjected to the processing in Step S14.

In Step S21, for example, the movement mode of the crystalline lens can be recognized based on, for example, at least one of the change of the position of the crystalline lens with respect to an eyeball and the change of the angle of the crystalline lens with respect to the eyeball. Similarly, the medical image processing method including Step S21 does not necessarily employ the foregoing components described in the embodiment or is not necessarily executed by these components.

As stated above, as processing of reducing abnormal values is performed, the position or the relative position of the second region obtained is relatively accurate so that the movement mode of the crystalline lens can be recognized more accurately.

Third Embodiment

Figure 6:
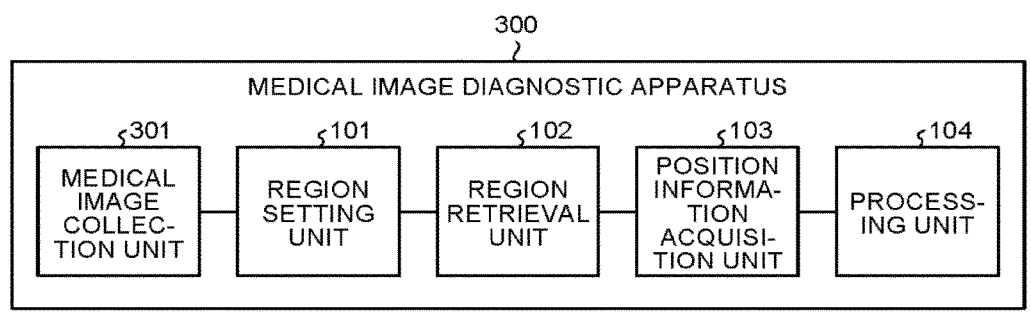
FIG. 6 is a block diagram showing the structure of a medical image diagnostic apparatus according to a third embodiment.

FIG. 6 is a block diagram showing the structure of a medical image diagnostic apparatus according to a third embodiment. FIG. 6 is a diagram showing the structure of a medical image diagnostic apparatus 300 according to the third embodiment, and the medical image diagnostic apparatus 300 includes a medical image collection unit 301, a region setting unit 101, a region retrieval unit 102, a position information acquisition unit 103 and a processing unit 104. Structurally and functionally identical to corresponding units shown in FIG. 1, the region setting unit 101, the region retrieval unit 102, the position information acquisition unit 103 and the processing unit 104 will not be described here repeatedly.

The medical image collection unit 301 is used to collect a plurality of chronological medical images corresponding to a region in a subject containing a specific structure. The medical image collection unit 301 can be realized as various medical scanning or imaging approaches.

Figure 7:
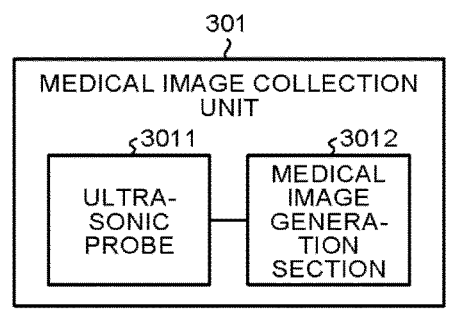
FIG. 7 is a block diagram showing the structure of an example of the medical image collection unit according to the third embodiment.

FIG. 7 is a block diagram showing an exemplary medical image collection unit according to the third embodiment. In an example, as shown in FIG. 7, the medical image collection unit 301 includes: an ultrasonic probe 3011 configured to perform ultrasonic scanning corresponding to the region containing the structure to acquire a reception signal corresponding to the region containing the structure; and a medical image generation section 3012 configured to generate a plurality of medical images based on the reception signal acquired by the ultrasonic probe 3011.

In addition, although not shown in FIG. 6, the movement recognition unit 201 described in the second embodiment may also be included in FIG. 6.

In other words, an ultrasonic diagnostic apparatus serving as the medical image diagnostic apparatus 300 is capable of carrying out, on the ultrasonic images, first tracking processing of tracking the chronological movement state of the eyeball region of a fetus, performing second tracking processing of determining erroneous tracking from the result of the first tracking processing and correcting the result, and re-tracking the chronological movement state of the eyeball region by using the result of the second tracking processing. By, as the second tracking processing, dividing the result of the first tracking processing into movement components orthogonal to each other and performing Fourier fitting on each of the components, the ultrasonic diagnostic apparatus performs removal of erroneous tracking based on the continuity of movement.

Apparently, some processing or methods are also disclosed in the foregoing description of the medical image diagnostic apparatus disclosed herein. When methods to be taken below do not overlap those described above, they will be described in detail below. It should be noted that these methods, although disclosed during the process of describing the medical image diagnostic apparatus, do not necessarily employ the foregoing components or are not necessarily executed by the foregoing components. For example, embodiments of the medical image diagnostic apparatus may be partially or totally implemented as hardware and/or firmware, and the medical image diagnostic method discussed below may also be wholly implemented as a computer-executable program, although these methods can also be implemented as the hardware and/or firmware of the medical image diagnostic apparatus.

Return to refer to FIG. 4, apart from Steps S11-S14, the medical image diagnostic method further includes, before Step S11, Step S31 of collecting a plurality of chronological medical images corresponding to the region in the subject containing the specific structure.

Further, in a case where the structure is the eyeball or the crystalline lens of a fetus in the subject, the medical image diagnostic method may further include the foregoing Step S21.

The medical image diagnostic apparatus or method according to the foregoing embodiment is capable of obtaining chronological images of a structure and automatically tracking the movement track of the structure accurately based on these images.

For the foregoing embodiment, the case has been described where each of the first region and the second region is set; however, embodiments are not limited to this. For example, a first region may be determined automatically based on the set second region. For example, when the area of an eyeball (or a crystalline lens) of a fetus is set, an area containing the set area and having a specific size may be set automatically.

For example, when the ultrasonic probe 3011 is a mechanical 4D probe capable of three-dimensional scanning or a 2D probe, because image data can be collected using volume data such that the specific structure is contained, only a second region representing the predetermined structure may be set and a first region may be set automatically based on the set second region. In an example, in a case where a second region is set in the area of a crystalline lens, an area containing the eyeball may be set automatically as a first region. In a case where first and second regions are kept contained in the volume data, the position information of the second region may be acquired without performing the foregoing correction processing.

For example, each step of the foregoing medical image processing method and the foregoing medical image diagnostic method and each component and/or unit of the foregoing medical image processing apparatus and the foregoing medical image diagnostic apparatus may be implemented as software, firmware, hardware or a combination thereof. In a case where the steps or modules and/or units are implemented through software or firmware, programs constituting software for realizing the foregoing methods may be installed on a computer having a dedicated hardware structure (e.g. an universal computer 800 shown in FIG. 8) from a memory medium or network, and the computer, when installed with various programs, is capable of realizing the functions of these programs.

FIG. 8 is a block diagram exemplifying the structure of a computer capable of realizing the embodiments. In FIG. 8, a central processing unit (namely, CPU) 801 executes various types of processing according to a program stored in a read-only memory (ROM) 802 or a program loaded to a random access memory (RAM) 803 from a memory part 808. The data needed by the CPU 801 to execute various types of processing may be stored in the RAM 803, if needed. The CPU 801, the ROM 802 and the RAM 803 are linked with each other via a bus line 804 with which an input/output interface 805 is also connected.

The following components are linked with the input/output interface 805: an input part 806 (including keyboard, mouse and the like); an output part 807 (including displays such as cathode ray tube (CRT), liquid crystal display (LCD) and loudspeaker), the memory part 808 (including hard disk and the like) and a communication part 809 (including a network interface card such as LAN card and modem). The communication part 809 carries out communication processing via a network such as the Internet. A driver 810 may also be linked with the input/output interface 805, if needed. If needed, a removable medium 811, for example, a magnetic disc, an optical disc, a magnetic optical disc, a semiconductor memory and the like, may be installed in the driver 810 to read a computer program therefrom and install the read computer program in the memory part 808 as needed.

In the case where the foregoing series of processing is achieved through software, programs forming the software are installed from a network such as the Internet or a memory medium such as the removable medium 811.

It should be appreciated by those skilled in the art that the memory medium is not limited to the removable medium 811 shown in FIG. 8 in which programs are stored and which are distributed separated from the apparatus to provide the programs to users. The removable medium 811 may be, for example, a magnetic disc (including floppy disc (registered trademark)), an optical disc (including compact disc read-only memory (CD-ROM) and digital versatile disk (DVD)), a magneto-optical disc (including mini disc (MD)(registered trademark)), and a semiconductor memory. Alternatively, the memory mediums may be the ROM 802, or the hard discs included in the memory part 808, in which programs are stored, and the programs may be distributed to users from the memory mediums.

The present application further provides a program product in which machine-readable instruction codes are stored. The foregoing medical image processing method and medical image diagnostic method according to the embodiments can be executed when the instruction codes are read and executed by a machine.

Accordingly, a memory medium for carrying the program product in which machine-readable instruction codes are stored can be also used as an embodiment. The memory medium includes, but is not limited to, a hard disc, an optical disc, a magneto-optical disc, a memory card, and a memory stick.

In the foregoing description of specific embodiments, the features described and/or shown for an implementation mode may be used in one or more other implementation modes in the same or like way or combined with those of other implementation modes, or may be replaced with those of other implementation modes.

It should be emphasized that the terms "comprise/include", as used herein, refer to the presence of a feature, an element, a step or a component but do not preclude the presence or addition of one or more other features, elements, steps or components.

In the above-described embodiments and examples, each step and/or unit are/is represented with a reference sign consisting of figures. It should be understood by those of ordinary skill in the art that the reference signs are merely intended to facilitate description and drawing but are not to be construed as limiting an order or any other aspect.

Furthermore, the methods of the present application may be implemented sequentially, synchronously or independently according to another time sequence, but not limited to being implemented according to the time sequence described herein. Therefore, the implementation order of the methods described herein is not to be construed as limiting the technical scope of the present application.

As described above, according to the first to third embodiments, improvement in the accuracy of analyzing the motion of a specific structure in medical images may be increased.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Through the foregoing description, the embodiments also provide the following technical solutions:

Appendix 1

A medical image processing apparatus, comprising:
a region setting unit configured to set, aiming at at least one of a plurality of chronological medical images corresponding to a region in a subject containing a specific structure, a first region containing the specific structure and a second region located in the first region and representing the specific structure;
a region retrieval unit configured to retrieve, based on the first and second regions set by the region setting unit, the first regions and the second regions in the rest of the medical images excluding those in which the first and second regions are set by the region setting unit;
a position information acquisition unit configured to acquire position information of the first region set by the region setting unit, position information of the first regions retrieved by the region retrieval unit, position information of the second region set by the region setting unit and position information of the second regions retrieved by the region retrieval unit; and
a processing unit configured to carry out, for at least part of the position information of the first region acquired by the position information acquisition unit, processing of reducing the abnormal values of the chronological change of the position information of the first region acquired by the position information acquisition unit and acquire, for each time point, the position information of the second region with respect to the position information of the first region containing the position information subjected to the processing.

Appendix 2

The medical image processing apparatus according to appendix 1, characterized in that
the structure is an eyeball or crystalline lens of a fetus in the subject; and
the first region is a region containing the eyeball or a region representing the eyeball.

Appendix 3

The medical image processing apparatus according to appendix 2, characterized in that the processing unit carries out processing of reducing the high frequency component of the chronological change of the position information of the first region as the processing of reducing the abnormal values of the chronological change of the position information of the first region.

Appendix 4

The medical image processing apparatus according to appendix 2, characterized in that the processing unit carries out processing through Fourier fitting aiming at the chronological change of the position information of the first region as the processing of reducing the abnormal values of the chronological change of the position information of the first region.

Appendix 5

The medical image processing apparatus according to appendix 2, characterized in that the region retrieval unit carries out the retrieval through template matching.

Appendix 6

The medical image processing apparatus according to appendix 2, characterized in that the position information acquisition unit takes the position information in a medical image obtained at a predetermined time point as reference position information and acquires the position information of the first regions and the second regions in the rest of medical images with respect to the reference position information.

Appendix 7

The medical image processing apparatus according to appendix 2, further comprising: a movement recognition unit configured to recognize, in a case where the structure is the crystalline lens, the movement mode of the crystalline lens based on the chronological change of the position information of the second region with respect to the position information of the first region containing the position information subjected to the processing of the processing unit.

Appendix 8

The medical image processing apparatus according to appendix 7, characterized in that the movement recognition unit recognizes the movement mode of the crystalline lens based on at least one of change of displacement of the crystalline lens with respect to the eyeball and change of angle of the crystalline lens with respect to the eyeball.

Appendix 9

The medical image processing apparatus according to appendix 2, characterized in that the medical images are ultrasonic images collected through ultrasonic diagnosis.

Appendix 10

A medical image diagnostic apparatus, comprising:
a medical image collection unit configured to collect a plurality of chronological medical images corresponding to a region in a subject containing a specific structure;
a region setting unit configured to set, aiming at at least one of the medical images, a first region containing the specific structure and a second region located in the first region and representing the specific structure;
a region retrieval unit configured to retrieve, based on the first and second regions set by the region setting unit, the first regions and the second regions in the rest of the medical images excluding those in which the first and second regions are set by the region setting unit;

a position information acquisition unit configured to acquire position information of the first region set by the region setting unit, position information of the first regions retrieved by the region retrieval unit, position information of the second region set by the region setting unit and position information of the second regions retrieved by the region retrieval unit; and a processing unit configured to carry out, for at least part of the position information of the first region acquired by the position information acquisition unit, processing of reducing the abnormal values of the chronological change of the position information of the first region acquired by the position information acquisition unit and acquire, for each time point, the position information of the second region with respect to the position information of the first region containing the position information subjected to the processing.

Appendix 11

The medical image diagnostic apparatus according to appendix 10, characterized in that the medical image collection unit comprises:

an ultrasonic probe configured to perform ultrasonic scanning corresponding to the region containing the structure to acquire a reception signal corresponding to the region containing the structure; and a medical image generation section configured to generate the medical images based on the reception signal acquired by the ultrasonic probe.

Appendix 12

A medical image processing method, comprising:

setting, aiming at at least one of a plurality of chronological medical images corresponding to a region in a subject containing a specific structure, a first region containing the specific structure and a second region located in the first region and representing the specific structure;

retrieving, based on the set first and second regions, the first regions and the second regions in the rest of the medical images excluding those in which the first and second regions are set;

acquiring position information of the set first region, position information of the retrieved first regions, position information of the set second region and position information of the retrieved second regions; and carrying out, for at least part of the position information of the first region acquired, processing of reducing the abnormal values of the chronological change of the position information of the first region and acquiring, for each time point, the position information of the second region with respect to the position information of the first region containing the position information subjected to the processing.

Appendix 13

The medical image processing method according to appendix 12, characterized in that the structure is an eyeball or crystalline lens of a fetus in the subject; and the first region is a region containing the eyeball or a region representing the eyeball.

Appendix 14

The medical image processing method according to appendix 13, characterized in that processing of reducing the frequency component of the chronological change of the position information of the first region is carried out as the processing of reducing the abnormal values of the chronological change of the position information of the first region.

Appendix 15

The medical image processing method according to appendix 13, characterized in that processing through Fourier fitting aiming at the chronological change of the position information of the first region is carried out as the processing of reducing the abnormal values of the chronological change of the position information of the first region.

Appendix 16

The medical image processing method according to appendix 13, characterized in that the retrieval through template matching is carried out.

Appendix 17

The medical image processing method according to appendix 13, characterized in that the position information in a medical image obtained at a predetermined time point is used as reference position information, and the position information of the first regions and the second regions in the rest of medical images with respect to the reference position information is acquired.

Appendix 18

The medical image processing method according to appendix 13, further comprising, in a case where the structure is the crystalline lens, recognizing the movement mode of the crystalline lens based on the chronological change of the position information of the second region with respect to the position information of the first region containing the position information subjected to the processing.

Appendix 19

The medical image processing method according to appendix 18, characterized in that the movement mode of the crystalline lens is recognized based on at least one of change of displacement of the crystalline lens with respect to the eyeball and change of angle of the crystalline lens with respect to the eyeball.

Appendix 20

The medical image processing method according to appendix 13, characterized in that the medical images are, for example, ultrasonic images collected through ultrasonic diagnosis.

Appendix 21

A medical image diagnostic method, comprising:

collecting a plurality of chronological medical images corresponding to a region in a subject containing a specific structure;

setting, aiming at at least one of the medical images, a first region containing the specific structure and a second region located in the first region and representing the specific structure;

retrieving, based on the set first and second regions, the first regions and the second regions in the rest of the medical images excluding those in which the first and second regions are set;

acquiring position information of the set first region, position information of the retrieved first regions, position information of the set second region and position information of the retrieved second regions; and carrying out, for at least part of the position information of the first region acquired, processing of reducing the abnormal values of the chronological change of the position information of the first region and acquiring, for each time point, the position information of the second region with respect to the position information of the first region containing the position information subjected to the processing.

Appendix 22

A computer program for realizing the medical image processing method of any one of appendixes 17 to 20 and the medical image diagnostic method of appendix 21.

Appendix 23

A computer-readable recording medium on which computer program codes for realizing the medical image processing method of any one of appendixes 17 to 20 and the medical image diagnostic method of appendix 21 are recorded.

According to the medical image processing apparatus, the medical image processing method, the medical image diagnostic apparatus, and the medical image diagnostic method disclosed herein, with the processing of reducing the abnormality of the chronological change of the first region containing the specific structure, the result of correcting the rough tracking is obtained and, based on the correction of the rough tracking, the more accurate change of the position information of the specific structure is obtained, which improves the accuracy of automated tracking.

What is claimed is:

1. A medical image processing apparatus, comprising:
processing circuitry configured to
set a first region of interest in at least one of a plurality of medical images;
carry out first tracking processing of tracking a motion of the first region of interest between the medical images and second tracking processing of tracking a motion of a second region of interest, different from the first region of interest, between the medical images, wherein the medical images contain an eyeball region of a fetus in a mother, the first region of interest contains the eyeball region of the fetus, and the second region of interest contains part of the eyeball region of the fetus; and
calculate the motion of the second region of interest with respect to the first region of interest by using a result of the first tracking processing and a result of the second tracking processing.

2. The medical image processing apparatus according to claim 1, wherein the processing circuitry is further configured to carry out first correction processing of correcting the result of the first tracking processing and second correction processing of correcting the result of the second tracking processing by using a result of the first correction processing, and calculate the motion of the second region of interest with respect to the first region of interest by using the result of the first correction processing and a result of the second correction processing.

3. The medical image processing apparatus according to claim 2, wherein the first correction processing includes dividing the result of the first tracking processing into a plurality of components and carrying out Fourier fitting on each of the components.

4. The medical image processing apparatus according to claim 3, wherein the second correction processing includes subtracting a corrected value obtained through the Fourier fitting from each of the components of the result of the second tracking processing.

5. The medical image processing apparatus according to claim 1, wherein the second region of interest contains at least part of a crystalline lens of the fetus in the medical image.

6. The medical image processing apparatus according to claim 5, wherein the processing circuitry is further configured to recognize a movement mode of the crystalline lens of the fetus contained in the second region of interest based on the motion of the second region of interest with respect to the first region of interest.

7. The medical image processing apparatus according to claim 6, wherein the processing circuitry is configured to recognize the movement mode based on at least one of a change of displacement of the crystalline lens and a change of the angle of the crystalline lens.

8. The medical image processing apparatus according to claim 1, wherein the medical images include an ultrasonic image obtained by transmitting and receiving ultrasound.

9. The medical image processing apparatus according to claim 1, wherein the processing circuitry is further configured to set the second region of interest in at least one of the medical images.

10. The medical image processing apparatus according to claim 1, wherein the processing circuitry is further configured to carry out retrieval of the first region of interest and the second region of interest in the medical images.

11. The medical image processing apparatus according to claim 1, wherein the processing circuitry is further configured to take positions of the first region of interest and the second region of interest in a medical image obtained at a predetermined time point as reference positions, and acquire information of the positions of the first region of interest and the second region of interest in medical images, excluding that obtained at the predetermined time point, with respect to the reference positions.

12. A medical image diagnostic apparatus, comprising:
processing circuitry configured to
collect a plurality of chronological medical images;
set a first region of interest in at least one of the medical images;
carry out first tracking processing of tracking a motion of the first region of interest between the medical images and second tracking processing of tracking a motion of a second region of interest, different from the first region of interest, between the medical images, wherein the medical images contain an eyeball region of a fetus in a mother, the first region of interest contains the eyeball region of the fetus, and the second region of interest contains part of the eyeball region of the fetus; and
calculate the motion of the second region of interest with respect to the first region of interest by using a result of the first tracking processing and a result of the second tracking processing.

13. A medical image processing method, comprising:
setting a first region of interest in at least one of a plurality of medical images;
carrying out first tracking processing of tracking a motion of the first region of interest between the medical images and second tracking processing of tracking a motion of a second region of interest, different from the first region of interest, between the medical images, wherein the medical images contain an eyeball region of a fetus in a mother, the first region of interest contains the eyeball region of the fetus, and the second region of interest contains part of the eyeball region of the fetus; and
calculating the motion of the second region of interest with respect to the first region of interest by using a result of the first tracking processing and a result of the second tracking processing.

\* \* \* \* \*